United States Patent [19]

Watson et al.

[11] 4,069,260

[45] Jan. 17, 1978

[54] PREPARATION OF UNSATURATED ALCOHOLS

[75] Inventors: Spencer C. Watson; Dennis B. Malpass; G. Scott Yeargin, all of Laporte, Tex.

[73] Assignee: Texas Alkyls, Inc., Deer Park, Tex.

[21] Appl. No.: 601,749

[22] Filed: Aug. 4, 1975

Related U.S. Application Data

[62] Division of Ser. No. 395,888, Sept. 10, 1973, abandoned.

[51] Int. Cl.² ............... C07C 29/00; C07C 33/02; C07C 33/06; C07C 33/10
[52] U.S. Cl. .................. 260/632 B; 252/522; 260/448 AD; 260/613 D; 260/618 R; 260/618 D; 260/632 R; 260/682
[58] Field of Search ........... 260/632 B, 618 R, 618 D, 260/613 D

[56] References Cited

U.S. PATENT DOCUMENTS

| 2,967,875 | 1/1961 | Wilke | 260/448 A |
|---|---|---|---|
| 3,024,287 | 3/1962 | Kennedy et al. | 260/632 B |
| 3,091,627 | 5/1963 | Rudner | 260/632 B |
| 3,238,237 | 1/1966 | Bedoit | 260/632 B |
| 3,631,065 | 12/1971 | Prendel et al. | 260/632 B |

Primary Examiner—Joseph E. Evans
Attorney, Agent, or Firm—Daniel C. Block

[57] ABSTRACT

This invention relates to the preparation of unsaturated alcohols useful as flavor and fragrance compounds. More specifically, this invention relates to the preparation of predominately cis-unsaturated alcohols by reacting a cis-1-alkenylaluminum dialkyl compound with an epoxide compound followed by hydrolysis. The alkenyl moiety has one or more double bond carbon-to-carbon linkage and from 5 to 20 carbon atoms that can be optionally substituted with the substituents selected from alkyl and aromatic radicals having 1 to 12 carbon atoms.

8 Claims, No Drawings

PREPARATION OF UNSATURATED ALCOHOLS

This is a division of application Ser. No. 395,888, filed Sept. 10, 1973 now abandoned.

BACKGROUND OF THE INVENTION

A number of unsaturated alcohols possess desirable organoleptic properties which make them useful in the preparation of flavor and fragrance intermediates. One such compound is the cis-isomer of 3-hexen-1-ol or "leaf alcohol" which possesses a pleasant, green aroma characteristic of new-mown grass. Originally, the compound was extracted from the leaves of green plants, but soon after the structure was determined, a synthetic procedure for the preparation of cis-3-hexen-1-ol was discovered and commercialized.

The starting material for the present day manufacture of cis-3-hexen-1-ol is butyne-1. The unsaturated alcohol was first synthesized by reacting butyne-1 with sodium or lithium in liquid ammonia to prepare butynylsodium, which was further reacted with 1,2-epoxyethane and hydrolyzed to yield the 3-hexyn-1-ol. This intermediate was then hydrogenated over palladium catalyst to yield the corresponding cis-3-hexen-1-ol. Due to its unavailability and low demand, butyne-1 is a very costly starting material. Thus, the economics of the production of the cis-3-hexen-1-ol is relatively expensive.

As hereinafter described, it is necessary to employ an unsaturated aluminum alkyl compound as an intermediate. The process for manufacturing these unsaturated aluminum alkyl intermediates has been previously reported. However, it has been found in practice that these unsaturated aluminum alkyl intermediate compounds are relatively unstable with respect to isomerization and decomposition, especially at higher temperatures. Thus, these prior art processes have proved to be unsatisfactory.

DETAILED DESCRIPTION OF THE INVENTION

In the practice of the present invention, the unsaturated alcohols of this invention are prepared by reaction of an appropriate predominately cis-1-alkenylaluminum dialkyl intermediate compound with an appropriate epoxide compound. The reaction of the cis-1-alkenylaluminum dialkyl with the epoxide can be conducted at any temperature between −80° and 200° C. The preferred temperature depends on the reactivity of the epoxide with the unsaturated aluminum dialkyl. Very reactive epoxides such as 1,2-epoxyethane and 1,2-epoxypropane require relatively low temperatures of reaction to avoid conditions which favor the polymerization of these epoxides to polyethers. Less reactive epoxides require prolonged reflux temperatures between 60°–130° C. to complete the reaction. The ideal range is between −80° and 130° C.

It has been found in practice that the epoxide compound will selectively react with the cis-1-alkenylaluminum dialkyl moiety to give a cis-dialkylaluminum-3-alken-1-oxide intermediate. That is to say, the epoxide will add to the vinyl carbon-aluminum bond only and will not react with the other two alkyl groups from the aluminum under the conditions as will hereinafter be described. Following this reaction step, the resulting cis-dialkylaluminum-3-alken-1-oxide is converted to the corresponding cis unsaturated alcohol with a dilute solution of aqueous acid. The resulting unsaturated alcohol will be provided with the following generic formula:

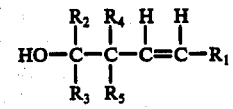

wherein $R_1$ is a straight-chained or branch-chained alkyl group having from 1 to 16 carbon atoms. Preferably, $R_1$ is a straight-chained or branch-chained alkyl group having from 1 to 8 carbon atoms. $R_2$, $R_3$, $R_4$ and $R_5$ can be the same or different and can each be selected from a group consisting of hydrogen, straight-or branch-chained alkyl groups having from 1 to 12 carbon atoms, and an aromatic radical having from 6 to 10 carbon atoms, which may be optionally substituted with an alkyl group having from 1 to 6 carbon atoms. It is preferred, however, that $R_2$ be hydrogen, $R_3$ be selected from hydrogen and lower alkyl having 1 to 6 carbon atoms, and $R_4$ and $R_5$ be selected from hydrogen, alkyl having from 1 to 6 carbon atoms, and phenyl.

The predominately cis-1-alkenylaluminum dialkyl compound used as an intermediate to manufacture the above-defined unsaturated alcohols will have the following formula:

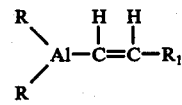

wherein R is a straight or branch-chained alkyl group having from 1 to 6 carbon atoms, and $R_1$ has been previously defined.

The above-defined predominately cis-1-alkenylaluminum dialkyl compound is prepared by the reaction of an appropriate trialkylaluminum compound with acetylene at a pressure of from atmospheric to about 15 psig.

At lower reaction temperatures (65° C or below) the cis-isomer is produced in 96–99% yield. As the temperature increases above 65° C., side reactions occur. Thus, in order to maintain a high cis- content, the temperature of this reaction should be maintained between about −80° and 65° C. and preferably between about −40° and 40° C.

It has been found in practice that the preparation of cis-unsaturated alcohols in up to 97–99% isomeric purity is possible by pre-coordination of the cis-1-alkenylaluminum dialkyl compounds with at least one molar equivalent of a suitable Lewis base. Preferred coordination agents are diethyl ether, diisopropyl ether, di-n-butyl ether, and especially preferred are the cyclic ethers and diethers, and aliphatic diethers and polyethers selected from tetrahydrofuran, tetrahydropyran, dioxane, 1,2-dimethoxyethane, 1,2-diethoxyethane, and the dimethyl ether of diethylene glycol. While these coordinating agents can also function as solvents, it is preferred to use cosolvents that include pentane, isopentane, petroleum ether, hexane, cyclohexane, heptane, benzene, toluene and xylene. The coordinating agent should be chosen carefully, since subsequent reaction with the epoxide compound may be hindered if the coordinating ether is much stronger than the reactant epoxide. Thus, the reaction product of a trialkylaluminum and acetylene is complexed with the above agents as soon as the reaction is complete. This will ensure a high cis-content in the resultant unsaturated alcohol by minimizing the formation of isomeric alcohols during the reaction of the epoxide with the unsaturated aluminum alkyl. The mode of addition preferred is unsaturated aluminum alkyl into the chosen Lewis base diluted with a suitable co-solvent. This is an exothermic process and the addition should be carried out with coolant applied to the mixture.

In addition to ensuring a high cis content in the resultant unsaturated alcohols, the coordinating agents also stabilize the unsaturated cis-1-alkenylaluminum dialkyl compounds to decomposition reactions provided at least a molar equivalent of coordinating agent is used.

The epoxide compounds can be selected from any number of epoxide compounds commercially available. In general, the epoxide compound will have the following generic formula:

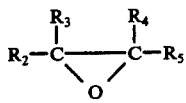

wherein $R_2$, $R_3$, $R_4$ and $R_5$ have been previously defined.

As noted above, the reaction between the cis-1-alkenylaluminum dialkyl compound and the epoxide provides an intermediate oxide which must be hydrolyzed. Thus, the solutions are hydrolyzed with dilute aqueous mineral acids to convert the resultant dialkyl-aluminum-3-alkenyl-1-oxide to the corresponding unsaturated alcohol. The aqueous mineral acids can be selected from sulfuric acid, nitric acid and phosphoric acid. There is a concomitant production of two moles of an alkane per mole of alcohol, and aluminium salts. The organic layer containing product solvent is separated, the aqueous layer is extracted several times more with solvent and the organic fractions combined. The solvent is removed by flash distillation usually under vacuum.

In order to illustrate the merits of the present invention, the following examples are provided.

EXAMPLE 1

A one-half gallon stirred autoclave equipped with cooling and heating coils was dried, purged with nitrogen, and charged with 3.0 moles of triethylaluminum. The triethylaluminum was heated to 35° C. and rapidly agitated while the reactor was pressured to 13 psig and continually fed with acetylene gas. After a period of 56 hours, a yellow slightly viscous liquid was obtained, which analysis showed to be 88 wt.% diethyl-1-butenylalumium by gas chromatography analysis of the resultant hydrolysis gases. A sample of this material was hydrolyzed with deuterium oxide 24 hours after preparation, and the corresponding 1-deutero-butene-1 was analyzed by proton magnetic resonance spectroscopy. Analysis showed the material to contain greater than 97% cis-1-deuterobutene-1.

To the stirred autoclave containing the 1-butenylaluminum diethyl was immediately added 342 grams of benzene solvent and the temperature lowered to 0° C by constant circulation of −10° C silicone fluid through the cooling coils. Gaseous 1,2-epoxyethane was slowly introduced above the surface of the liquid at a rate such that the reaction exotherm never rose above 5° C. After 3 hours of feeding, the reaction exotherm ceased after the addition of approximately 2.9 moles of 1,2-epoxyethane and the reaction was assumed to be complete. The product solution was then slowly hydrolyzed by addition to 2 liters of 10% sulfuric acid. The organic layer separated cleanly and was withdrawn. The aqueous layer was re-extracted three more times with 200 ml. portions of ether which were later combined with the original organic layer. The ether and benzene were removed in a flash evaporator and the crude product transferred to a still containing a 3 ft. packed distillation column equipped with a partial take-off head. Under vacuum distillation at 27 mm pressure approximately 116 grams of 3-hexen-1-ol were obtained boiling between 70°–73° C. The material was analyzed by gas chromatography and showed a content of 67.8% cis-3-hexen-1-ol. The overall yield of 3-hexen-1-ol was approximately 27% based on cis-1-butenylaluminum diethyl

EXAMPLE 2

The experiment described in Example 1 was repeated with the exception that the 1-butenylaluminum diethyl was prepared at 65° C. instead of 35° C. with a resulting yield of 82 wt.%, diethyl-1-butenylaluminum. When a sample of this material was treated with $D_2O$ the 1-deutero-butene-1 obtained possessed a cis-isomer content of approximately 90%. The reduction in cis content was also reflected in the final product, cis-3-hexen-1-ol. Only 67 grams of 3-hexen-1-ol boiling between 69°–72° C. were obtained which analysis showed to contain 56% cis-3-hexen-1-ol. The overall yield of cis-3-hexen-1-ol was 13% based on cis-1-butenylaluminum diethyl.

EXAMPLE 3

The experiment described in Example 1 was repeated after a 6-month time-lapse between the synthesis of the 1-butenylaluminum diethyl and the reaction step with 1,2-epoxyethane. Approximately 1.0 mole of 1-butenylaluminum diethyl in 145 grams of benzene was treated with 48.4 grams of 1,2-epoxyethane at 0°–5° C. After hydrolysis and fractional distillation under vacuum there was obtained 29 grams of product which possessed a cis-isomer content of 63%. The overall yield of cis-3-hexen-1-ol based on cis-1-butenylaluminum diethyl was 20%.

EXAMPLE 4

A quantity (1.5 mole) of 1-butenylaluminum diethyl was prepared as described in Example b 1. The material was then diluted with 400 grams of n-hexane and removed from the reactor. In a clean one-half gallon autoclave was placed 400 grams hexane and 280 grams of 1,2-epoxyethane. The temperature of the solution was maintained at −10° C. while the solution of 1-butenylaluminum diethyl in n-hexane was slowly fed to the reactor at a rate such that the reactor temperature never rose above 0° C. After the 1-butenylaluminum diethyl had been charged the material was immediately hydrolyzed as described in Example 2 and product fractionally distilled at 27 mm pressure. Approximately 29 grams of material boiling between 71°–73° were obtained. Gas analysis showed the material to be approximately 95% cis-3-hexen-1-ol. The overall yield of cis-3-hexen-1-ol based on cis-1-butenylaluminum diethyl was 18%.

EXAMPLE 5

The same general reaction conditions in Example 4 were repeated with the exception that diisopropyl ether was used as the solvent for the 1,2-epoxyethane (1.56 mole). Neat cis-1-butenylaluminum diethyl (1.0 mole) was added in small portions by syringe to the solution in the temperature range 5°–8° C. The mixture was stirred overnight at ambient temperature and worked up as above. In this case approximately 45 grams of 3-hexen-1-ol boiling between 71°–72° C. at 23 mm were obtained. The product had a cis-isomer content of 80%. The overall yield of cis-3-hexen-1-ol was 33% based on 1-butenylaluminum diethyl.

EXAMPLE 6

Following essentially the same procedure as in Example 1, except that a benzene-tetrahydrofuran (THF) co-solvent system was employed, another preparation of cis-3-hexen-1-ol was attempted. Thus, to a solution consisting of 351.9 g. (2.51 mole) of cis-1-butenylaluminum diethyl, 264 g. (3.66 mole) of THF and 1.5 liters of dry benzene was charged 131 g. (2.97 mole) of gaseous 1,2-epoxyethane in the vapor phase over a period of 3 hours at 10°–15° C. The mixture was stirred overnight at ambient temperature, then hydrolyzed and worked up in the usual manner. A total of 117.5 grams of distillate was collected boiling at 67.3°–69.5° C. at 20 mm Hg. Analysis by GC showed the product to be 97% cis. The yield of cis-3-hexen-1-ol was 45% based on cis-1-butenylaluminum diethyl. Elemental analysis showed 71.89% C, 12.06% H and 16.20% O (theory for cis-3-hexen-1-ol: 71.95% C, 12.08% H, 15.97% O).

EXAMPLE 7

Another preparation of cis-3-hexen-1-ol was carried out following essentially the same general procedure as in Example 6, except that 1,2-dimethoxyethane was used as the coordinating agent for cis-1-butenylaluminum diethyl and ethylene oxide addition was carried out at 0°–5° C. The usual work-up afforded a 47% yield of cis-3-hexen-1-ol which was analyzed by gas chromatography and found to contain 96% cis-3-hexen-1-ol.

EXAMPLE 8

Using p-dioxane as the coordinating agent for diethyl butenylaluminum, another preparation of 3-hexen-1-ol was attempted employing the same general procedure of Example 6. Ethylene oxide addition was conducted at 0°–8° C. A 43% yield of cis-3-hexen-1-ol was realized which contained 95% cis-3-hexen-1-ol.

EXAMPLE 9

A quantity of 1-butenylaluminum diethyl (1.0 mole) was prepared as previously described in Example 1. The material was diluted to form a 20 wt.% solution in benzene-THF (82%-18%). 1,2-Epoxyethane was also diluted to form a 20 wt.% solution in benzene. A continuous reactor apparatus was built to allow direct contact of the two streams containing dilute solutions of the aluminum alkyl and the 1,2-epoxyethane. The 1-butenylaluminum diethyl and 1,2-epoxyethane streams were fed to a mixing-tee at a rate of 5.0 grams per minute, and allowed to flow through 12 feet of ⅛inch tubing which was submerged in a dry ice-silicone oil bath maintained at 0° C. The product (diethylaluminum 3-hexen-1-oxide) from the tubular reactor was immediately hydrolyzed as described in Example 1 and extraction and fractional distillation were performed to isolate the product. Approximately 52 grams of 3-hexen-1-ol was produced boiling between 17°–73° C. at 27 mm pressure. Cis-isomer content of the product was 97%. The overall yield of cis-3-hexen-1-ol based on 1-butenylaluminum was 50%.

EXAMPLE 10

To the stirred autoclave described in Example 1 was charged 3.0 moles of tri-n-butylaluminum. The autoclave was pressured to 13 psig with acetylene gas and the pressure maintained while the mixture heated to 35° C. and rapidly stirred. Reaction was allowed to proceed with constant acetylene feed for 24 hours. Gas chromatographic analysis of the hydrolysis gases showed the resultant unsaturated aluminum alkyl composition to be 83 wt.% 1-hexenylaluminum di-n-butyl. This material was diluted by the addition of 670 grams of benzene and a 50% molar excess of THF and further reacted with 1,2-epoxyethane by the procedure described in Example 6. A total of 3.1 moles (10% excess) of 1,2-epoxyethane were introduced into the gas phase of the autoclave while the reaction temperature was maintained 0°–5° C. After epoxide addition was complete, the reaction mixture was stirred at ambient temperature overnight. The material was then hydrolyzed, extracted and fractionally distilled as described in Example 1. The main distillation fraction recovered 152 grams of material boiling at 37°–38° C. at 0.2 mm Hg pressure. The material was identified as 3-octen-1-ol by its infrared and proton magnetic resonance spectra and elemental analysis (calculated for 3-octen-1-ol — 74.94%C, 12.58% H, 12.48% O; found — 75.09% C, 12.51% H and 12.48% O). The cis-isomer content of this fraction was approximately 85%. The overall yield of cis-3-octene-1-ol based on 1-hexenylaluminum di-n-butyl was 34%. The alcohol possessed a distinctly floral aroma.

EXAMPLE 11

To the stirred autoclave described in Example 1, was placed 3.0 moles of triisobutylaluminum. This was allowed to react with acetylene at 13 psig pressure for 24 hours at 35° C. to give 81 wt.% (4-methyl-1-pentenyl) aluminum diisobutyl. This material was diluted with 670 grams of benzene and a 50% molar excess of THF and 3.1 mole of 1,2-epoxyethane were introduced slowly to the gas phase while the temperature was maintained at 0°–5° C. The reaction mixture was stirred overnight at ambient temperature. The resulting product after hydrolysis, extraction and fractional isomer (b.p. 69°–70° C. at 5 mm Hg) content was 85%. The overall yield of cis-6-methyl-3-hepten-1-ol was 20% based on the (4-methyl-1-pentyl) aluminum diisobutyl.

EXAMPLE 12

This example illustrates the effect of higher temperature on the isomer distribution in the unsaturated aluminum alkyl as evidenced by the lower yield of cis unsaturated alcohol final product.

Following essentially the same procedure as in Example 9, except that the intermediate (4-methyl-1-pentenyl) aluminum diisobutyl was heated to ca. 110°–120° C for approximately 15 minutes before the benzene and THF were added, a 2.6% yield of cis-6-methyl-3-hepten-1-ol (b.p. 81°–83° C at 10 mm Hg) was isolated.

EXAMPLE 13

In the stirred autoclave described in Example 1 was placed 3.0 moles of tri-n-hexylaluminum. This aluminum alkyl was reacted with acetylene gas at 35° under a constant 13 psig pressure for a period of 37 hours. Analysis revealed the material to be composed approximately 83 wt.% 1-octenylaluminum di-n-hexyl. This material was diluted with 924 grams of benzene and reacted slowly with 137 grams of gaseous 1,2-epoxyethane as previously described in Example 8, at 0°–5° C. Hydrolysis, extration and fractional distillation of the product yielded 186 grams of a material boiling between 108°–110° C. at 0.4 mm. The product was identified to be 3-decen-1-ol and contained a cis-isomer content of approximately 65%. The overall yield of cis-3-decen-1-ol was 26% based on 1-octenylaluminum di-n-hexyl.

EXAMPLE 14

The experiment in Example 11 was repeated beginning with 3.0 moles of tri-2-methylpentylaluminum. After 24 hours reaction at 35° C. with acetylene gas at 13 psig, the material was sampled and analysis showed 84 wt.% cis-(4-methyl-1-heptenyl) aluminum di-2-methylpentyl. This material was then diluted with 924 grams of benzene and slowly reacted with 3.1 moles of gaseous 1,2-epoxyethane while the temperature maintained between 0°–5° C.

Hydrolysis, extraction and fractional distillation produced 380 grams of material boiling between 75°–78° C. at 4 mm which was identified by gas chromatography, infrared and proton magnetic resonance spectroscopy to 6-methyl-3-nonen-1-ol. The cis-isomer content was found to be 67%. The overall yield of cis-6-methyl-3-nonen-1-ol based on (4-methyl-1-heptenyl) aluminum di-1,2-methylpentyl was 32%.

EXAMPLE 15

The experiment in Example 11 was repeated beginning with 3.0 moles of tri-4-methylpentylaluminum. After 36 hours at 35° C. with an acetylene overpressure of 13 psig, the material analyzed as 82% cis-(6-methyl-1-heptenyl) aluminum di-4-methylpentyl. This material was subsequently dluted with benzene and reacted with ca. 3.1 moles of 1,2-epoxyethane at 0°–5° C. Work-up in the usual manner afforded 165 grams of product boiling between 70°–73° C. at 4 mm which was identified by gas chromatography, and infrared analysis to be cis-8-methyl-3-nonen-1-ol. The cis-isomer content was ca. 67%. The overall yield of cis-8-methyl-3-nonen-1-ol based on (6-methyl-1-heptenyl) aluminum di-4-methylpentyl was 23%.

EXAMPLE 16

To 2.29 moles of 1-butenylaluminum diethyl-1in 1.3 liters benzene prepared as described in Example 1, was slowly added 2.69 moles of 1,2-epoxypropane at 28°–35° C. The solution was stirred for 15 hours at 35° C. and 1 hour at 60° C., then hydrolyzed, extracted and fractionally distilled from solvent to yield 84 grams of a product boiling at 59°–60° C. at 10 mm pressure. Material was identified by gas chromatographic, infrared and proton nuclear magnetic resonance spectroscopy, and elemental analysis to be cis-4-hepten-2-ol with a cis-isomer content of approximately 85%. Elemental analysis revealed 73.72% C, 12.39% H, and 14.07% O (calculated for 4-hepten-2-ol 73.63% C, 12.36% H and 14.01% O). The product obtained had a pleasant "balsam like" odor. The overall yield of cis-4-hepten-2-ol was 27% based on 1-butenyl-aluminum diethyl.

EXAMPLE 17

A freshly prepared batch of cis-1-butenylaluminum dialkyl was used to prepare solutions with tetrahydrofuran with varying molar ratios. The solutions and control sample were analyzed periodically for composition of hydrolysis gases. The results are compiled in Table I below.

TABLE I

| Elapsed Time (Days) | Normalized Mole Percent of Butene-1 in Hydrolysis Gases Sample | | | | |
|---|---|---|---|---|---|
| | Control* | 0.65** | 1.49** | 2.00** | 2.99** |
| 0 | 32.2 | 29.6 | 31.9 | 27.7 | 30.4 |
| 28 | 28.5 | 28.3 | 25.9 | 22.8 | 27.2 |
| 94 | 25.0 | 28.5 | 12.9 | 12.9 | 14.7 |
| 184 | 18.3 | 29.5 | 6.9 | 3.8 | 5.1 |

*Freshly prepared cis-1-butenylaluminum diethyl
**Molar ratio of cis-1-butenylaluminum diethyl to THF The results shows a stabilizing influence by the presence of at least 1 mole equivalent of tetrahydrofuran per mole of cis-1-butenylaluminum dialkyl as evidenced by the near constant mole percentage of butene-1 in the 0.65 molar ratio solution. The solution with ratios greater than one showed a faster decomposition rate than even the control sample, indicating that at least 1 mole equivalent of coordinating agent per mole of unsaturated aluminum alkyl is necessary.

As can be seen from the above examples and description, the unsaturated alcohols can be prepared in any one of several ways, including:

1. A solution ranging from 5–60% by weight of the cis-1-alkenylaluminum dialkyl prepared and slowly mixed with a solution ranging from 10–50% by weight of the 1,2-epoxide in a suitable solvent system. The 1,2-epoxide is added to the cis-1-alkenylaluminum dialkyl in stoichiometric excess to the extent of 5–20%.

2. A solution ranging from 5–60% by weight of the cis-1-alkenylaluminum dialkyl is prepared and the 1,2-epoxide is slowly fed as a liquid or gas to the reaction mixture.

3. A solution ranging from 10–60% by weight of the 1,2-epoxide is prepared. A solution ranging from 5–60% by weight of the cis-1-alkenylaluminum dialkyl is then slowly added to this. The 1,2-epoxide is maintained in 10–400% stoichiometric excess.

4. Solutions ranging from 5–60% by weight of the 1,2-epoxide and the cis-1-alkenylaluminum dialkyl are fed continuously to a mixing vessel where they are brought into intimate contact in stoichiometric molar ratios ranging from 1:4 to 4:1.

5. Any of the above methods 1–4 in which the unsaturated aluminum alkyl is coordinated with ether prior to reaction with the epoxide compound.

What is claimed is:

1. A process of preparing a predominately cis-unsaturated alcohol having the following formula:

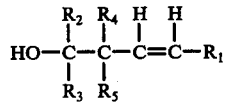

wherein $R_1$ is a straight or branched chain alkyl group having 1 to 16 carbon atoms, $R_2$, $R_3$, $R_4$ and $R_5$ can be the same or different and are selected from hydrogen, a straight or branched chain alkyl group having 1 to 12 carbon atoms, an aryl radical having 6 to 10 carbon atoms, said aryl radical can be substituted with an alkyl group having 1 to 6 carbon atoms, an alkoxy radical having 1 to 6 carbon atoms and halogen; comprising the steps of:

a. pre-coordinating a predominately cis-1-alkenyl aluminum dialkyl compound having the following formula:

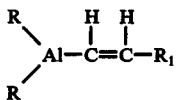

wherein R can be selected from lower alkyl having 1 to 6 carbon atoms and $R_1$ has been previously defined; with at least one molar equivalent of a Lewis base, b. reacting said product of step (a) with an epoxide compound having the following formula:

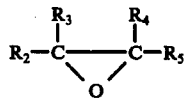

wherein $R_2$, $R_3$, $R_4$ and $R_5$ have been previously defined, said reaction being carried out at a temperature of between $-80°$ C. and $130°$ C.;

c. treating the reaction product of steps (a) and (b) with an aqueous solution of a mineral acid, to yield the cis-unsaturated alcohol compounds.

2. The process of claim 1 wherein $R_1$ is selected from a straight or branched chain alkyl group having from 2 8 carbon atoms, $R_2$ and $R_3$ is hydrogen, $R_4$ and $R_5$ can be selected from lower alkyl having 1 to 6 carbon atoms and phenyl.

3. The process of claim 1 wherein the coordinating Lewis base is selected from ether, diether, polyether, cyclic ether or cyclic diether.

4. The process of claim 3 wherein the coordinating agent is selected from diethyl ether, diisopropyl ether, di-n-butyl ether, tetrahydrofuran, tetrahydropyran, dioxane, 1,2-dimethoxyethane, 1,2-diethoxyethane, dimethyl ether of diethylene glycol, and mixtures thereof.

5. The process of claim 4 wherein the coordinating agent is selected from tetrahydrofuran, tetrahydropyran, dioxane, and 1,2-dimethoxyethane.

6. The process of claim 1 wherein the coordinating agent is contained in a cosolvent selected from pentane, isopentane, petroleum ether, hexane, cyclohexane, heptane, benzene, toluene, xylene, and mixtures thereof.

7. The process of claim 1 wherein the cis-1-alkenylaluminum compound is prepared by:

a. reacting a compound having the following formula:

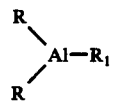

wherein R and $R_1$ have been previously defined; with b. acetylene at a pressure of between 0 and 15 psig and at a temperature of between $-80°$ C. and $70°$ C.;

c. coordinating the reaction product of steps a) and b) with a coordinating agent.

8. The process of claim 1 wherein the cis-unsaturated alcohol is cis-3-hexen-1-ol that is formed by reacting i. cis-1-butenylaluminum diethyl, with
ii. gaseous 1,2-epoxyethane
iii. at a temperature of between 10° and 15° C. in the presence of a mixture of benzene and tetrahydrofuran;
iv. treating the reaction product of (i) and (ii) with sulfuric acid.
v. recovering cis-3-hexen-1-ol.

* * * * *